United States Patent
Teh et al.

(10) Patent No.: US 7,816,488 B2
(45) Date of Patent: Oct. 19, 2010

(54) METHOD TO ESTIMATE PENT VALUES

(75) Inventors: Joo Wooi Teh, Calgary (CA); Joyce Lai-Ching Chau, Calgary (CA); Victoria Ker, Calgary (CA); Gary Yim, Calgary (CA)

(73) Assignee: Nova Chemicals (International) S.A. (CH)

( * ) Notice: Subject to any disclaimer, the term of this patent is extended or adjusted under 35 U.S.C. 154(b) by 347 days.

(21) Appl. No.: 12/150,569

(22) Filed: Apr. 29, 2008

(65) Prior Publication Data

US 2008/0276717 A1  Nov. 13, 2008

(30) Foreign Application Priority Data

May 11, 2007  (CA)  .................................... 2588352

(51) Int. Cl.
C08F 6/00  (2006.01)
G01N 25/18  (2006.01)
G01N 29/04  (2006.01)
C08F 10/02  (2006.01)

(52) U.S. Cl. ............................. 528/503; 374/43; 73/799
(58) Field of Classification Search ................ 528/503; 374/43; 73/799
See application file for complete search history.

(56) References Cited

U.S. PATENT DOCUMENTS

| | | | |
|---|---|---|---|
| 3,879,368 A | 4/1975 | Johnson | |
| 4,011,382 A | 3/1977 | Levine et al. | |
| 4,719,193 A | 1/1988 | Levine et al. | |
| 5,434,116 A | 7/1995 | Sone et al. | |
| 5,554,775 A | 9/1996 | Krishnamurti et al. | |
| 5,637,659 A | 6/1997 | Krishnamurti et al. | |
| 5,733,987 A | 3/1998 | Covezzi et al. | |
| 5,783,512 A | 7/1998 | Jacobsen et al. | |
| 5,834,393 A | 11/1998 | Jacobsen et al. | |

(Continued)

FOREIGN PATENT DOCUMENTS

WO  WO 02/074818 A1  9/2002

OTHER PUBLICATIONS

Peri et al, The Surface Structure of Silica Gel, The Journal of Physical Chemistry, Aug. 1968, vol. 72, pp. 2926-2933.

(Continued)

*Primary Examiner*—Fred M Teskin
(74) *Attorney, Agent, or Firm*—Kenneth H. Johnson

(57) ABSTRACT

The PENT value for a resin may be estimated within ±10% by determining the % of heat flow to melt a fraction of a polymer above or below a set point and comparing it to a graph or algorithm of PENT values related to the % of heat flow to melt entire sample for a number of resins made using the same catalyst system. In a similar manner one may estimate the process conditions to prepare a polymer having a target PENT value based on the conditions used to prepare the samples for the graph or algorithms. The invention provides a simple procedure that may be used at a manufacturing site to estimate PENT values.

12 Claims, 3 Drawing Sheets

U.S. PATENT DOCUMENTS

| | | | |
|---|---|---|---|
| 6,087,293 | A | 7/2000 | Carnahan et al. |
| 6,935,185 | B2 | 8/2005 | Corleto |
| 2007/0298508 | A1 * | 12/2007 | DesLauriers et al. .......... 436/85 |

OTHER PUBLICATIONS

Noshay et al, Transition Metal Catalyzed Polymerizations, 1988, Cambridge University Press, NY, pp. 396-416.

Pullukat et al, Silica-Based Ziegler-Natta Catalysts: A Patent Review, Catal. Rev. Sci. Eng. 1999, vol. 41(3&4), pp. 389-428.

Xie et al, Gas Phase Ethylene Polymerization: Production Processes, Polymer Properties, and Reactor Modeling, Ind. Eng. Chem. Res., 1994, vol. 33, pp. 449-479.

Rolf Mulhaupt, Macromol. Chem. Phys., 2003, vol. 204, No. 2, pp. 289-327.

Boussie et al, A Fully Integrated High-Throughput Screening Methodology . . . , J. Am. Chem. Soc., 2003, vol. 125, pp. 4306-4317.

\* cited by examiner

METHOD TO ESTIMATE PENT VALUES

FIELD OF THE INVENTION

The present invention relates to a method to an accelerated method to estimate the PENT value of a resin, particularly a high density polyethylene copolymer.

BACKGROUND OF THE INVENTION

There are a number of regulations relating to pressure pipe made from polymers and in particular polyethylene. There are a number of ASTM methods for testing the crack growth and the strength of pipe under stress (ASTM F1474 (corresponding to ISO 13479), D2837; and D1598), additionally there is the Pennsylvania Notched Impact test (PENT) (ASTM F 1473). Generally, the industry associations and government regulators specify a PENT value for pressurized pipe made from a resin. To determine a value for the PENT test a pipe is extruded from the resin and then subjected to a long term pressure test. The time to do this test may be in the order of thousands of hours. In the manufacture of pipe for these applications manufacturers rely on the manufacturing specifications and regular testing of resins to assure that resins made within the manufacturing specification will meet a required PENT value. There is a need for a simple relatively quick test procedure that can be carried out at a manufacturing site to determine (estimate within 10%) the PENT value of a resin.

U.S. Pat. No. 6,935,185 issued Aug. 30, 2005 in the name of Corleto, assigned to Fina Technology, Inc. discloses an accelerated method to determine the failure time of a polyethylene using a notched stress test and determining the minimum displacement rate for the polymer. This is the point at which there is slow crack growth due to crazing at the tip of the notch. The patent teaches away from the present disclosure as it does not teach or suggest a differential scanning calorimetery (DSC) method to predict PENT values.

The present invention provides a relatively simple procedure to predict a PENT value for a resin with a high degree of certainty. (e.g. 90% certainty).

SUMMARY OF THE INVENTION

The present invention provides a process to predict the PENT value of a resin prepared using a specific catalyst system comprising determining the PENT values for a number of different resins prepared using the specific catalyst system, determining for each of the resins for which a PENT value was determined one or more of:

1) the percent of the heat capacity to melt the fraction of the polymer over the range from 90° C. to a set point relative to melting the entire sample at a heat up rate of 15 to 25° C. per minute which sample has been conditioned by successive self nucleation and annealing over the temperature range from 30 to 150° C. by heating and cooling the sample at a fixed rate from 70 to 95° C. per minute over the temperature range in decreasing increments of upper temperature from 5 to 10° C. provided that at least one increment is the set point; and 2) the percent of the heat capacity to melt the fraction of the polymer over the range from a set point to 140° C. relative to melting the entire sample at a heat up rate of 15 to 25° C. per minute which sample has been conditioned by successive self nucleation and annealing over the temperature range from 30 to 150° C. by heating and cooling the sample at a fixed rates from 70 to 95° C. per minute over the temperature range in decreasing increments of upper temperature from 5 to 10° C. provided that at least one increment is the set point; and plotting the results of the % heat capacity of 1, 2 or both as a function of the PENT values to generate a calibration curve.

The present invention further provides a method to select initial set point operating conditions for a plant producing polyolefin resins for use in pressure pipe applications comprising determining the PENT value for the resin according to the above process, and then from the operating conditions used to generate the resins for the PENT plot selecting conditions which are expected to generate the resin having the required PENT value.

DETAILED DESCRIPTION

Figure 2:
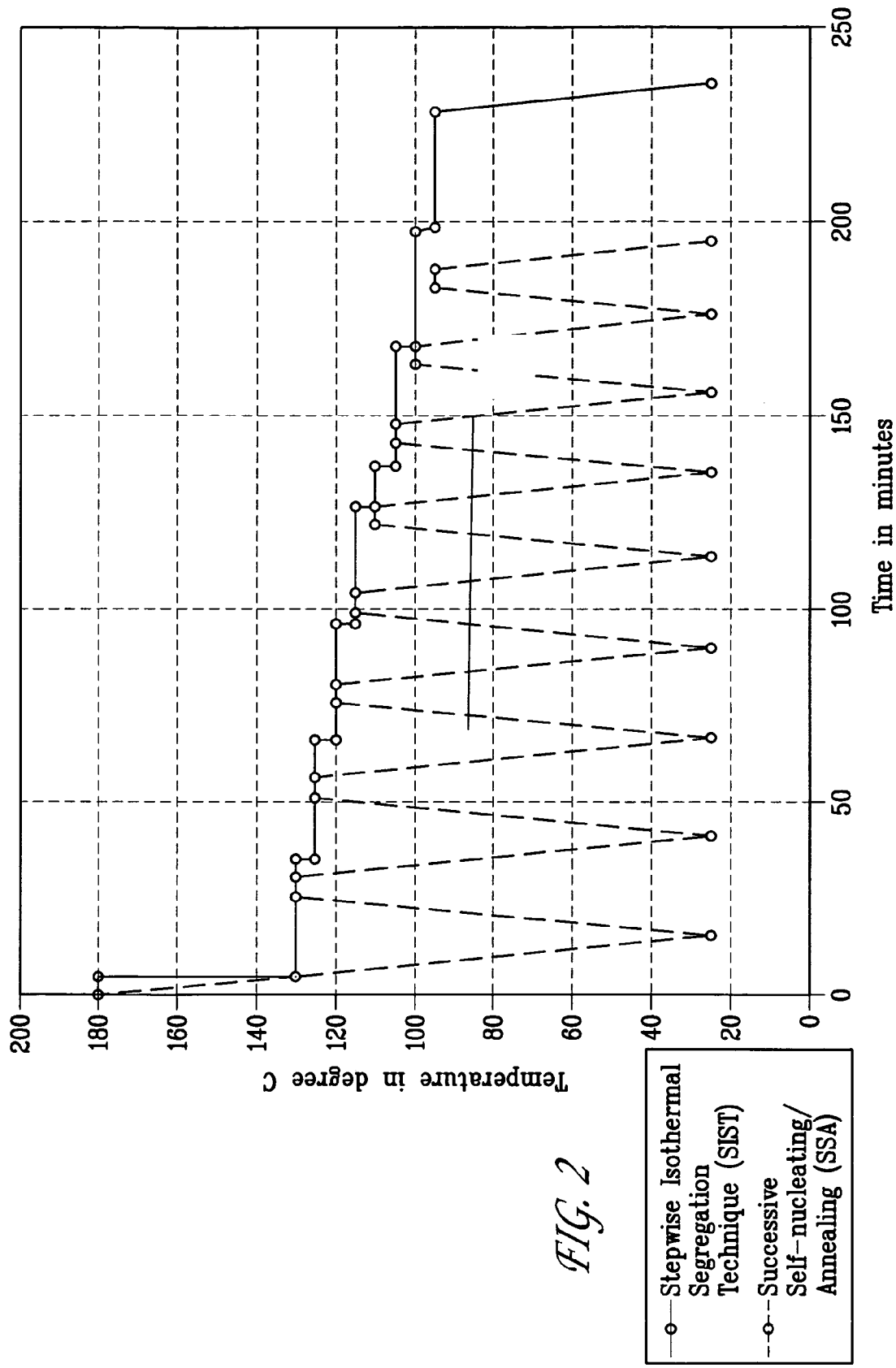
FIG. 2 is a schematic representation of a successive self nucleation and annealing procedure.

As used in this specification the phrase successive self nucleation and annealing refers to a process in which a sample of polymer is initially melted and then cooled at a constant fairly rapid rate to standardize or re set the heat history of the sample. Then the sample is subjected to a number of successive heating and cooling cycles at constant heat up, annealing and constant cool down rates below the "melting temperature" of the sample decreasing in maximum temperature by from 5° C. to 10° C. from the prior high temperature. One such cycle is illustrated in FIG. 2.

The PENT test and similar tests are a measure of the long term "toughness" of a polymer. Its is generally understood that the toughness of a polymer is a function of a number of structural and morphological parameters. Without being bound by theory, it is believed one of the morphological and structural properties of the polymer that will have an impact on toughness is the number and distribution of short chain branches in the polymer. However, the number and distribution of short chain branches in a sample of polymer will also lead to different components of the polymer having different crystallization temperatures (melting points). Using Differential Scanning Calorimetery (DSC) methods it is possible to separate a sample of a resin into components having a different crystallization temperature. Then if the sample is melted at a constant heat up rate it is possible to determine the heat capacity attributable to the relative components. Then the relative amount of the component may be related to the PENT value either in the form of a graph or algorithm.

When a sample of polymer which has been subjected to successive self nucleation and annealing is melted at a constant heat up rate, the fractions or components of polymer which melt at different temperatures will take up heat as the temperature rise passes through each temperature differential of the successive self nucleation and annealing step. If a plot of heat flow (W/g) versus temperature is made as the polymer is heated there are a number of peaks and valleys with increasing temperature.

If the number of cycles in the successive self nucleation and annealing step is from 6 to 15, preferably 8 to 12, most preferably 8 to 10 and the heat up and cool down rate for each step is at a constant rate from 75° C. to 85° C., preferably from 78° C. to 82° C., most preferably 80° C. and the annealing time at each temperature is from 5 to 10 minutes, preferably 6 to 8, most preferably 7 minutes when the sample is melted at a constant heat up rate from 15° C. to 25° C., preferably 18° C. to 22° C., most preferably 20° C. and a plot is made of heat flow (mW/g) and temperature there will be a number of peaks and valleys in the plot. At the lower temperatures of up to about 115° C. the peaks and valleys are relatively rounded and the difference between peaks and valleys is not sharp or substantial. Somewhere in the temperature range from 115° C. to 125° C., typically from 118° C. to 122.5° C. desirably from 119.5° C. to 121.5° C. there will be a valley followed by a peak in which the relative height of the peak (i.e. from the adjacent "valley" to the adjacent peak) is greater than about 2 W/g. The inflection point at the bottom of the valley is taken to be the set point for the process of the invention. If the successive self nucleation and annealing step did not have a temperature limit corresponding to the inflection point then the successive self nucleation and annealing should be repeated with one of the temperatures corresponding to the inflection point. Then when the melting step is conducted there will be a clear demarcation at the inflection point. The modern DSC machines will be able to integrate the heat input (heat flow up to the inflection point and over the whole curve to give the % of heat capacity to melt the component(s) either up to or beyond the inflection or set point.

In a further embodiment of the invention the heat flow curve generated by the differential scanning calorimeter may be converted to an algorithm. The algorithm may be derived using a simple computerized curve fitting method. In a further embodiment the algorithm may include other polymer properties such as flow rate of the polymer under various loads (e.g. $I_2$, $I_{10}$, $I_{21}$, etc.). For example the algorithm could be related to the flow rate or flow index ($I_2$ as determined by the ASTM method D 1238-04c (190/2.16). One such equation is:

$$\text{Ln (predicted PENT value)} = a + bx^3 + cy \text{ wherein}$$

a, b, and c are constants derived from the curve fitting the data; x is the flow rate or flow index of the polymer (190/2.16) and y is the percentage of heat flow for melting the polymer above 120° C. or preferably above 127° C. Typically for chrome catalyst on clay supports a is from about 20 to 25, preferably from about 23 to 24; b is from −0.00050 to −00060 and c is from about −0.3 to about −0.3.

In a further embodiment the algorithm may include a term for melt strength. The algorithm is of the form $\text{PENT} = e^{(a+bx+cy+dz)}$ wherein a, b, c, x and y are as defined above and d is the Rosland Melt strength measured at 200° C. in cN. In this equation for the same catalyst system a is typically from 18 to 20, preferably from 18.5 to 19.5; b is from −0.140 to −0.155, typically from −0.145 to −0.150; c is from −0.20 to −0.30, typically from −0.21 to −0.23; and d is from 0.050 to 0.060, typically from 0.0525 to 0.0535.

Typically the resin or polymer will be a polyolefin. Generally the polyolefin will have a density greater than 0.940 g/cc, typically from 0.940 to 0.960, preferably from 0.945 to 0.955 g/cc. The polymer may comprise from 95 to 99.9 weight % of ethylene and from 0.1 to 5 weight % of one or more $C_{4-8}$ alpha olefin monomers. Some $C_{4-8}$ alpha olefins are 1-butene, 1-hexene and 1-octene.

The comparisons of the present invention are narrow. The resin or polymer must be produced using the same catalyst system. As used herein, catalyst system refers to the active catalyst species, the support if required and the activator if required. Additionally, Applicants do not recommend including resins made using different process platforms in the process of the present invention. For polyolefins there are typically three or four processes, gas phase (including both fluidized bed and stirred bed), slurry and solution processes.

Solution and slurry polymerization processes are well known in the art. The monomers and optionally hydrogen are generally dissolved in an inert hydrocarbon solvent. Typically the inert hydrocarbon solvent, may be a $C_{5-12}$ hydrocarbon which may be unsubstituted or substituted by a $C_{1-4}$ alkyl group such as pentane, hexane, heptane, octane, cyclohexane, methylcyclohexane or hydrogenated naphtha. An additional solvent is Isopar® E ($C_{8-12}$ aliphatic solvent) sold by Exxon Chemical Co.).

The polymerization may be conducted at temperatures from about 20° C. to about 250° C. Depending on the product being made, this temperature may be relatively low such as from 20° C. to about 120° C. for a slurry process and from 120° C. to 250° C. for the solution process. The pressure of the reaction may be as high as about 15,000 psig for the older high pressure processes or may range from about 15 to 4,500 psig.

Gas phase polymerization of olefins and particularly alpha olefins has been known for at least about 30 years. Generally a gaseous mixture comprising from 0 to 15 mole % of hydrogen, from 0 to 30 mole % of one or more $C_{3-8}$ alpha olefins, from 15 to 100 mole % of ethylene, and from 0 to 75 mole % of nitrogen and/or a non-polymerizable hydrocarbon at a temperature from 50° C. to 120° C., preferably from 60° C. to 120° C., most preferably from 75° C. to about 110° C., and at pressures typically not exceeding 3,500 KPa (about 500 psi), preferably not greater than 2,400 KPa (about 350 psi) are polymerized in the presence of a supported catalyst system typically in a single rector.

The gas phase process may be a fluidized bed process or a stirred bed process. In a fluidized bed process the velocity of the recycle gas stream through the bed is sufficiently high to fluidize the bed. This is more fully described for example at lines 30 to 40 of Column 7 of U.S. Pat. No. 4,011,382 issued Mar. 8, 1977 to Levine et al. assigned to Union Carbide Corporation.

The catalyst system may be supported on an inorganic or refractory support, including for example alumina, silica and clays or modified clays or an organic support (including polymeric support such as polystyrene or cross-linked polystyrene). The catalyst support may be a combination of the above components. However, preferably the catalyst is supported on an inorganic support or an organic support (e.g. polymeric) or mixed support. Some refractories include silica, which may be treated to reduce surface hydroxyl groups and alumina. The support or carrier may be a spray-dried silica. Generally the support will have an average particle size from about 0.1 to about 1,000, preferably from about 10 to 150 microns. The support typically will have a surface area of at least about 10 $m^2/g$, preferably from about 150 to 1,500 $m^2/g$. The pore volume of the support should be at least 0.2, preferably from about 0.3 to 5.0 ml/g.

Generally the refractory or inorganic support may be heated at a temperature of at least 200° C. for up to 24 hours, typically at a temperature from 500° C. to 800° C. for about 2 to 20, preferably 4 to 10 hours. The resulting support will be essentially free of adsorbed water (e.g. less than about 1 weight %) and may have a surface hydroxyl content from about 0.1 to 5 mmol/g of support, preferably from 0.5 to 3 mmol/g.

A silica suitable for use in the present invention has a high surface area and is amorphous. For example, commercially available silicas are marketed under the trademark of Sylopol® 958 and 955 by Davison Catalysts, a Division of W. R. Grace, and Company and ES-70W sold by Ineos Silica.

The amount of the hydroxyl groups in silica may be determined according to the method disclosed by J. B. Peri and A. L. Hensley, Jr., in *J., Phys. Chem.*, 72 (8), 2926, 1968, the entire contents of which are incorporated herein by reference.

While heating is the most preferred means of removing OH groups inherently present in many carriers, such as silica, the OH groups may also be removed by other removal means, such as chemical means. For example, a desired proportion of OH groups may be reacted with a suitable chemical agent, such as a hydroxyl reactive aluminum compound (e.g. triethyl aluminum) or a silane compound. This method of treatment has been disclosed in the literature and two relevant examples are: U.S. Pat. No. 4,719,193 to Levine in 1988 and Noshay A. and Karol F. J. in *Transition Metal Catalyzed Polymerizations*, Ed. R. Quirk, 396, 1989. For example the support may be treated with an aluminum compound of the formula $Al((O)_a R^1)_b X_{3-b}$ wherein a is either 0 or 1, b is an integer from 0 to 3, $R^1$ is a $C_{1-8}$ alkyl radical, and X is a chlorine atom. The amount of aluminum compound is such that the amount of aluminum on the support prior to adding the remaining catalyst components will be from about 0 to 2.5 weight %, preferably from 0 to 2.0 weight % based on the weight of the support.

The clay type supports are also preferably treated to reduce adsorbed water and surface hydroxyl groups. However, the clays may be further subject to an ion exchange process, which may tend to increase the separation or distance between the adjacent layers of the clay structure.

The catalyst for the polymerization may comprise a Phillips type chromium (Cr) catalyst, a Ziegler-Natta catalyst or a bulky ligand single site catalyst and conventional activators/co-catalysts. Ziegler-Natta catalysts have been reviewed in the literature by a number of authors. In particular, reviews by Pullukat, T. J. and Hoff, R. E in Catal. Rev. Sci. Eng., 41(3&4), 389-428, 1999 and Xie, T.; McAuley, K. B.; Hsu, J. C. C. and Bacon, D. W. in Ind. Eng. Chem. Res., 33, 449-479, 1994 and references within give a good understanding what is meant by a Ziegler-Natta catalyst. Other authors have described single site catalysts. In particular, reviews by Mülhaupt, R. Macromol. Chem. Phys. 2004, 289-327, 2003 and Boussie, T. R. et al. in J. Am. Chem. Soc., 125, 4306-4317, 2003 and references within give a good understanding by what is meant by single site catalysts.

The chromium based catalysts may be chromium oxide or silyl chromate on a support as described below. The oxide catalysts are typically prepared by contacting the support with a solution comprising an inorganic (e.g. $Cr(NO_3)_3$) or an organic (e.g. chromium acetate) chromium compound. The bis hyrdrocarbyl component may be a trialkyl compound (e.g. trimethyl) or a tri aryl compound (e.g. tribenzyl). The supported compound is then recovered, dried and oxidized. The inorganic chromium catalysts and chromium acetate type catalysts are air oxidized at elevated temperature (e.g. 400 to 800° C.) to activate them. The silyl chromate type catalysts (e.g. bis hydrocarbyl silyl chromate) are not oxidized and are activated with aluminum. If the support does not contain aluminum or titanium the catalyst may be activated with aluminum compounds described below for the Ziegler Natta catalysts (e.g. tri alkyl aluminums and dialkyl aluminum halides preferably chlorides). The chromium catalyst may also be a chromocene catalyst as described for example in U.S. Pat. No. 3,879,368 issued Apr. 22, 1975 to Johnson assigned to Union Carbide Corporation.

Typically, the Ziegler-Natta catalysts comprise a support, a magnesium compound (optionally in the presence of a halide donor to precipitate magnesium halide), a titanium compound and an aluminum compound, in the presence of an electron donor. The aluminum compound may be added at several stages. It may be added to the support to chemically treat it and/or it may be added at some later point during the manufacture of the catalyst.

Typically the Ziegler-Natta catalyst comprise an aluminum compound of the formula $R^1{}_b Al(OR^1)_a X_{3-(a+b)}$ wherein a is an integer from 0 to 3, b is an integer from 0 to 3 and the sum of a+b is from 0 to 3, $R^1$ is the same or different $C_{1-10}$ alkyl radical and X is a chlorine atom, a transition metal, preferably a titanium compound of the formula $Ti((O)_c R^2)_d X_e$ wherein $R^2$ is selected from the group consisting of $C_{1-4}$ alkyl radicals, $C_{6-10}$ aromatic radicals and mixtures thereof, X is selected from the group consisting of a chlorine atom and a bromine atom, c is 0 or 1, d is 0 or an integer up to 4 and e is 0 or an integer up to 4 and the sum of d+e is the valence of the Ti atom, a magnesium compound of the formula $(R^5)_f Mg\ X_{2-f}$ wherein each $R^5$ is independently a $C_{1-8}$ alkyl radical and f is 0, 1 or 2; $CCl_4$ or an alkyl halide selected from the group consisting of $C_{3-6}$ secondary or tertiary alkyl halides, and optionally an electron donor, a molar ratio of total Al to Ti (e.g. the first and/or second aluminum additions (if two additions are made) $Al^1$ and $Al^2$—typically if two additions are made from 0 to 60 weight % of the aluminum compound may be used to treat the support and the remaining aluminum is added at some time during the rest of the catalyst synthesis) from 2:1 to 15:1 a molar ratio of Al from the second aluminum ($Al^2$) addition to Ti from 1:1 to 8:1; a molar ratio of Mg:Ti from 0.5:1 to 20:1, preferably 1:1 to 12:1; a molar ratio of active halide (this excludes the halide from the Al and Ti compounds) from the $CCl_4$ or alkyl halide to Mg from 1:1 to 6:1, preferably 1.5:1 to 5:1; and a molar ratio of electron donor to Ti from 0:1 to 18:1, preferably from 1:1 to 15:1.

The catalyst components may be reacted in an organic medium such as an inert $C_{5-10}$ hydrocarbon that may be unsubstituted or is substituted by a $C_{1-4}$ alkyl radical. Some solvents include pentane, iso-pentane, hexane, isohexane, heptane, octane, cyclohexane, methyl cyclohexane, hydrogenated naphtha and ISOPAR® E (a solvent available from Exxon Chemical Company) and mixtures thereof.

Typically the aluminum compounds useful in the formation of the catalyst or catalyst precursor have the formula $R^1{}_b Al(OR^1)_a X_{3-(a+b)}$ wherein a is an integer from 0 to 3, b is an integer from 0 to 3 and the sum of a+b is from 0 to 3, $R^1$ is the same or different $C_{1-10}$ alkyl radical and X is a chlorine atom. Suitable aluminum compounds include, trimethyl aluminum (TMA), triethyl aluminum (TEAL), isoprenyl aluminum, tri-isobutyl aluminum (TiBAL), diethyl aluminum chloride (DEAC), tri-n-hexyl aluminum (TnHAl), tri-n-octyl aluminum (TnOAl), diethyl aluminum ethoxide and mixtures thereof. The aluminum compounds containing a halide may be an aluminum sesqui-halide. Preferably, in the aluminum compound a is 0, b is 3 and $R^1$ is a $C_{1-8}$ alkyl radical.

The magnesium compound may be a compound of the formula $(R^5)_f MgX_{2-f}$ wherein each $R^5$ is independently selected from the group consisting of $C_{1-8}$ alkyl radicals and f is 0, 1 or 2. Some commercially available magnesium compounds include magnesium chloride, butyl octyl magnesium, dibutyl magnesium and butyl ethyl magnesium. If the magnesium compound is soluble in the organic solvent it may be used in conjunction with a halogenating agent or reactive organic halide to form magnesium halide (i.e. $MgX_2$ where X is a halogen preferably chlorine or bromine, most preferably chlorine), which precipitates from the solution (potentially forming a substrate for the Ti compound). Some halogenating agents include $CCl_4$ or a secondary or tertiary halide of the formula $R^6Cl$ wherein $R^6$ is selected from the group consisting of secondary and tertiary $C_{3-6}$ alkyl radicals. Suitable chlorides include sec-butyl chloride, t-butyl chloride and sec-propyl chloride. The reactive halide is added to the catalyst in a quantity such that the active Cl:Mg molar ratio should be from 1.5:1 to 5:1, preferably from 1.75:1 to 4:1, most preferably from 1.9:1 to 3.5:1.

The titanium compound in the catalyst may have the formula $Ti((O)_cR^2)_dX_e$ wherein $R^2$ is selected from the group consisting of $C_{1-4}$ alkyl radicals, $C_{6-10}$ aromatic radicals and mixtures thereof, X is selected from the group consisting of a chlorine atom and a bromine atom, c is 0 or 1, d is 0 or an integer up to 4 and e is 0 or an integer up to 4 and the sum of d+e is the valence of the Ti atom. If c is 1 the formula becomes $Ti(OR^2)_dX_e$ wherein $R^2$ is selected from the group consisting of $C_{1-4}$ alkyl radicals, and $C_{6-10}$ aromatic radicals, X is selected from the group consisting of a chlorine atom and a bromine atom, preferably a chlorine atom, d is 0 or an integer up to 4 and e is 0 or an integer up to 4 and the sum of d+e is the valence of the Ti atom. The titanium compound may be selected from the group consisting of $TiCl_3$, $TiCl_4$, $Ti(OC_4H_9)_4$, $Ti(OC_3H_7)_4$, and $Ti(OC_4H_9)Cl_3$ and mixtures thereof. Most preferably, the titanium compound is selected from the group consisting of $Ti(OC_4H_9)_4$ and $TiCl_4$ and mixtures thereof. Generally, the titanium in the catalyst or catalyst precursor is present in an amount from 0.20 to 5, preferably from 0.20 to 4, most preferably from 0.25 to 3.5 weight % based on the final weight of the catalyst (including the support).

The catalyst system may be prepolymerized prior to being fed to the reactor. This process is well known to those skilled in the art. For example Basell WO 02/074818 A1 and Montel U.S. Pat. No. 5,733,987 disclose such processes. By prepolymerizing the weight ratios of the components in the catalyst or catalyst precursor while initially within the above ranges may be reduced due to the presence of the formed prepolymer.

The electron donor may be selected from the group consisting of $C_{3-18}$ linear or cyclic aliphatic or aromatic ethers, ketones, esters, aldehydes, amides, nitriles, amines, phosphines or siloxanes. Preferably, the electron donor is selected from the group consisting of diethyl ether, triethyl amine, 1,4-dioxane, tetrahydrofuran, acetone, ethyl acetate, and cyclohexanone and mixtures thereof. The electron donor may be used in a molar ratio to the titanium from 0:1 to 18:1 preferably in a molar ratio to Ti from 3:1 to 15:1, most preferably from 3:1 to 12:1.

In the catalyst or catalyst precursor the molar ratio of Mg:Ti may be from 0.5:1 to 20:1, preferably from 1:1 to 12:1, most preferably from 1:1 to 10:1. If a second aluminum addition is used the molar ratio of second aluminum ($Al^2$) to titanium in the catalyst may be from 1:1 to 8:1, preferably from 1.5:1 to 7:1, most preferably from 2:1 to 6:1. Generally, from 0 to not more than about 60 weight %, preferably from 10 to 50 weight %, of the aluminum (compound in the catalyst) may be used to treat the support (e.g. $Al^1$). The molar ratio of active halide (from the alkyl halide or $CCl_4$) to Mg may be from 1.5:1 to 5:1 preferably from 1.75:1 to 4:1, most preferably from 1.9:1 to 3.5:1. The molar ratio of electron donor, if present, to Ti may be from 1:1 to 15:1, most preferably from 3:1 to 12:1.

The Ziegler-Natta catalyst may be activated with one or more co-catalysts of the formula $Al(R^7)_{3-g}X_g$ wherein $R^7$ is a $C_{1-6}$ alkyl radical, X is a chlorine atom and g is 0 or 1 and mixtures thereof. The co-catalyst may be selected from the group consisting of tri $C_{1-6}$ alkyl aluminums, alkyl aluminum chlorides (e.g. di $C_{1-6}$ alkyl aluminum chloride), and mixtures thereof. This includes, but is not limited to, trimethyl aluminum, triethyl aluminum, tri propyl aluminum, tributyl aluminum, tri isobutyl aluminum, isoprenylaluminum, n-hexyl aluminum, diethyl aluminum chloride, dibutyl aluminum chloride, and mixtures thereof. A preferred co-catalyst is triethyl aluminum.

The co-catalyst may be fed to the reactor, preferably a gas phase reactor to provide from 10 to 130, preferably 10 to 80 more preferably from 15 to 70, most preferably from 20 to 60 ppm of aluminum (Al ppm) based on the polymer production rate.

The catalyst may be a bulky ligand single site catalyst. Such catalysts are generally used in slurry or gas phase reactors on a support as described above.

The bulky ligand single site catalysts may have the formula

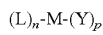

$(L)_n\text{-M-}(Y)_p$ wherein M is selected from the group consisting of Ti, Zr, and Hf; L is a monoanionic ligand independently selected from the group consisting of cyclopentadienyl-type ligands, and a bulky heteroatom ligand containing not less than five atoms in total (typically of which at least 20%, preferably at least 25% numerically are carbon atoms) and further containing at least one heteroatom selected from the group consisting of boron, nitrogen, oxygen, phosphorus, sulfur and silicon, said bulky heteroatom ligand being sigma or pi-bonded to M, Y is independently selected from the group consisting of activatable ligands; n may be from 1 to 3; and p may be from 1 to 3, provided that the sum of n+p equals the valence state of M, and further provided that two L ligands may be bridged for example by a silyl radical or a $C_{1-4}$ alkyl radical, or a mixture thereof.

The term "cyclopentadienyl" refers to a 5-member carbon ring having delocalized bonding within the ring and typically being bound to the active catalyst site, generally a group 4 metal (M) through $\eta^5$-bonds. The cyclopentadienyl ligand may be unsubstituted or up to fully substituted with one or more substituents independently selected from the group consisting of $C_{1-10}$ hydrocarbyl radicals which hydrocarbyl substituents are unsubstituted or further substituted by one or more substituents independently selected from the group consisting of a halogen atom and a $C_{1-4}$ alkyl radical; a halogen atom; a $C_{1-8}$ alkoxy radical; a $C_{6-10}$ aryl or aryloxy radical; an amido radical which is unsubstituted or substituted by up to two $C_{1-8}$ alkyl radicals; a phosphido radical which is unsubstituted or substituted by up to two $C_{1-8}$ alkyl radicals; silyl radicals of the formula $-Si-(R)_3$ wherein each R is independently selected from the group consisting of hydrogen, a $C_{1-8}$ alkyl or alkoxy radical, and $C_{6-10}$ aryl or aryloxy radicals; and germanyl radicals of the formula $Ge-(R)_3$ wherein R is as defined above.

Typically the cyclopentadienyl-type ligand is selected from the group consisting of a cyclopentadienyl radical, an indenyl radical and a fluorenyl radical which radicals are unsubstituted or up to fully substituted by one or more substituents independently selected from the group consisting of a fluorine atom, a chlorine atom; $C_{1-4}$ alkyl radicals; and a phenyl or benzyl radical which is unsubstituted or substituted by one or more fluorine atoms.

In the formula above if none of the L ligands is bulky heteroatom ligand then the catalyst could be a mono cyclopentadienyl (Cp) catalyst, a bridged or unbridged bis Cp catalyst or a bridged constrained geometry type catalysts or a tris Cp catalyst.

If the catalyst contains one or more bulky heteroatom ligands the catalyst would have the formula:

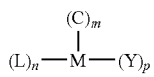

wherein M is a transition metal selected from the group consisting of Ti, Hf and Zr; C is a bulky heteroatom ligand preferably independently selected from the group consisting of phosphinimine ligands (as described below) and ketimide ligands (as described below); L is a monoanionic ligand independently selected from the group consisting of cyclopentadienyl-type ligands; Y is independently selected from the group consisting of activatable ligands; m is 1 or 2; n is 0 or 1; and p is an integer and the sum of m+n+p equals the valence state of M, provided that when m is 2, C may be the same or different bulky heteroatom ligands.

For example, the catalyst may be a bis(phosphinimine), a bis (ketimide), or a mixed phosphinimine ketimide dichloride complex of titanium, zirconium or hafnium. Alternately, the catalyst could contain one phosphinimine ligand or one ketimide ligand, one "L" ligand (which is most preferably a cyclopentadienyl-type ligand) and two "Y" ligands (which are preferably both chloride).

The preferred metals (M) are from Group 4 (especially titanium, hafnium or zirconium) with titanium being most preferred. In one embodiment the catalysts are group 4 metal complexes in the highest oxidation state.

The catalyst may contain one or two phosphinimine ligands (PI) that are bonded to the metal. The phosphinimine ligand is defined by the formula:

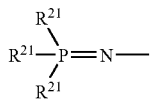

wherein each $R^{21}$ is independently selected from the group consisting of a hydrogen atom; a halogen atom; $C_{1-20}$, preferably $C_{1-10}$ hydrocarbyl radicals which are unsubstituted by or further substituted by a halogen atom; a $C_{1-8}$ alkoxy radical; a $C_{6-10}$ aryl or aryloxy radical; an amido radical; a silyl radical of the formula:

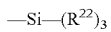

wherein each $R^{22}$ is independently selected from the group consisting of hydrogen, a $C_{1-8}$ alkyl or alkoxy radical, and $C_{6-10}$ aryl or aryloxy radicals; and a germanyl radical of the formula:

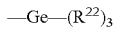

wherein $R^{22}$ is as defined above.

The preferred phosphinimines are those in which each $R^{21}$ is a hydrocarbyl radical, preferably a $C_{1-6}$ hydrocarbyl radical, such as a t-butyl radical.

Suitable phosphinimine catalysts are Group 4 organometallic complexes that contain one phosphinimine ligand (as described above) and one ligand L that is either a cyclopentadienyl-type ligand or a heteroatom ligand.

As used herein, the term "ketimide ligand" refers to a ligand which:

(a) is bonded to the transition metal via a metal-nitrogen atom bond;

(b) has a single substituent on the nitrogen atom (where this single substituent is a carbon atom which is doubly bonded to the N atom); and (c) has two substituents Sub 1 and Sub 2 (described below) which are bonded to the carbon atom.

Conditions a, b and c are illustrated below:

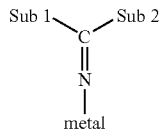

The substituents "Sub 1" and "Sub 2" may be the same or different. Exemplary substituents include hydrocarbyls having from 1 to 20, preferably from 3 to 6, carbon atoms, silyl groups (as described below), amido groups (as described below) and phosphido groups (as described below). For reasons of cost and convenience it is preferred that these substituents both be hydrocarbyls, especially simple alkyls radicals and most preferably tertiary butyl radicals.

Suitable ketimide catalysts are Group 4 organometallic complexes that contain one ketimide ligand (as described above) and one ligand L that is either a cyclopentadienyl-type ligand or a heteroatom ligand.

The term bulky heteroatom ligand is not limited to phosphinimine or ketimide ligands and includes ligands that contain at least one heteroatom selected from the group consisting of boron, nitrogen, oxygen, phosphorus, sulfur or silicon. The heterbatom ligand may be sigma or pi-bonded to the metal. Exemplary heteroatom ligands include silicon-containing heteroatom ligands, amido ligands, alkoxy ligands, boron heterocyclic ligands and phosphole ligands, as all described below.

Silicon containing heteroatom ligands are defined by the formula:

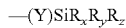

wherein the — denotes a bond to the transition metal and Y is sulfur or oxygen.

The substituents on the Si atom, namely $R_x$, $R_y$ and $R_z$ are required in order to satisfy the bonding orbital of the Si atom. The use of any particular substituent $R_x$, $R_y$ or $R_z$ is not especially important to the success of this invention. It is preferred that each of $R_x$, $R_y$ and $R_z$ is a $C_{1-2}$ hydrocarbyl group (i.e. methyl or ethyl) simply because such materials are readily synthesized from commercially available materials.

The term "amido" is meant to convey its broad, conventional meaning. Thus, these ligands are characterized by (a) a metal-nitrogen bond; and (b) the presence of two substituents (which are typically simple alkyl or silyl groups) on the nitrogen atom.

The terms "alkoxy" and "aryloxy" is also intended to convey its conventional meaning. Thus, these ligands are characterized by (a) a metal oxygen bond; and (b) the presence of a hydrocarbyl group bonded to the oxygen atom. The hydrocarbyl group may be a $C_{1-10}$ straight chained, branched or cyclic alkyl radical or a $C_{6-13}$ aromatic radical which radicals are unsubstituted or further substituted by one or more $C_{1-4}$ alkyl radicals (e.g. 2,6 di-tertiary butyl phenoxy).

Boron heterocyclic ligands are characterized by the presence of a boron atom in a closed ring ligand. This definition includes heterocyclic ligands that may also contain a nitrogen atom in the ring. These ligands are well known to those skilled in the art of olefin polymerization and are fully described in the literature (see, for example, U.S. Pat. Nos. 5,637,659; 5,554,775; and the references cited therein).

The term "phosphole" is also meant to convey its conventional meaning. "Phospholes" are cyclic dienyl structures having four carbon atoms and one phosphorus atom in the closed ring. The simplest phosphole is $C_4PH_4$ (which is analogous to cyclopentadiene with one carbon in the ring being replaced by phosphorus). The phosphole ligands may be substituted with, for example, $C_{1-20}$ hydrocarbyl radicals (which may, optionally, contain halogen substituents); phosphido radicals; amido radicals; or silyl or alkoxy radicals. Phosphole ligands are also well known to those skilled in the art of olefin polymerization and are described as such in U.S. Pat. No. 5,434,116 (Sone, to Tosoh).

The term "activatable ligand" (i.e. "Y" in the above formula) or "leaving ligand" refers to a ligand that may be activated by the aluminoxane (also referred to as an "activator") to facilitate olefin polymerization. Exemplary activatable ligands are independently selected from the group consisting of a hydrogen atom; a halogen atom, preferably a chlorine or fluorine atom; a $C_{1-10}$ hydrocarbyl radical, preferably a $C_{1-4}$ alkyl radical; a $C_{1-10}$ alkoxy radical, preferably a $C_{1-4}$ alkoxy radical; and a $C_{5-10}$ aryl oxide radical; each of which said hydrocarbyl, alkoxy, and aryl oxide radicals may be unsubstituted by or further substituted by one or more substituents selected from the group consisting of a halogen atom, preferably a chlorine or fluorine atom; a $C_{1-8}$ alkyl radical, preferably a $C_{1-4}$ alkyl radical; a $C_{1-8}$ alkoxy radical, preferably a $C_{1-4}$ alkoxy radical; a $C_{6-10}$ aryl or aryloxy radical; an amido radical which is unsubstituted or substituted by up to two $C_{1-8}$, preferably $C_{1-4}$ alkyl radicals; and a phosphido radical which is unsubstituted or substituted by up to two $C_{1-8}$, preferably $C_{1-4}$ alkyl radicals.

The number of activatable ligands (Y) depends upon the valence of the metal and the valence of the activatable ligand. The preferred catalyst metals are Group 4 metals in their highest oxidation state (i.e. 4+) and the preferred activatable ligands are monoanionic (such as a halide—especially chloride or $C_{1-4}$ alkyl—especially methyl).

The bulky ligand transition metal complex may have the formula: $[(Cp)_nM[N=P(R^{21})]_mY_p$ wherein M is the transition (group 4) metal; Cp is a $C_{5-13}$ ligand containing a 5-membered carbon ring having delocalized bonding within the ring and bound to the metal atom through covalent $\eta^5$ bonds and said ligand being unsubstituted or up to fully 4 substituted with one or more substituents selected from the group consisting of a halogen atom, preferably chlorine or fluorine; $C_{1-4}$ alkyl radicals; and benzyl and phenyl radicals which are unsubstituted or substituted by one or more halogen atoms, preferably fluorine; $R^{21}$ is a substituent selected from the group consisting of $C_{1-6}$ straight chained or branched alkyl radicals, $C_{6-10}$ aryl and aryloxy radicals which are unsubstituted or may be substituted by up to three $C_{1-4}$ alkyl radicals, and silyl radicals of the formula —Si—(R)$_3$ wherein R is $C_{1-4}$ alkyl radical or a phenyl radical; Y is selected from the group consisting of a leaving ligand; n is 1 or 2; m is 1 or 2; and the valence of the transition metal–(n+m)=p.

For the single site type catalyst the activator may be a complex aluminum compound of the formula $R^{12}{}_2AlO(R^{12}AlO)_qAlR^{12}{}_2$ wherein each $R^{12}$ is independently selected from the group consisting of $C_{1-20}$ hydrocarbyl radicals and q is from 3 to 50, and optionally a hindered phenol to provide a molar ratio of Al:hindered phenol from 2:1 to 5:1 if the hindered phenol is present;

In the aluminum compound preferably, $R^{12}$ is a methyl radical and q is from 10 to 40.

The single site catalysts aluminum activator (MAO) systems may have a molar ratio of aluminum from the aluminoxane to transition metal from 5:1 to 1000:1, preferably from 10:1 to 500:1, most preferably from 30:1 to 300:1, most desirably from 50:1 to 120:1.

The single site catalyst systems may also be activated with an ionic activator selected from the group consisting of:

(A) compounds of the formula $[R^{13}]^+[B(R^{14})_4]^-$ wherein B is a boron atom, $R^{13}$ is a cyclic $C_{5-7}$ aromatic cation or a triphenyl methyl cation and each $R^{14}$ is independently selected from the group consisting of phenyl radicals which are unsubstituted or substituted with a hydroxyl group or with 3 to 5 substituents selected from the group consisting of a fluorine atom, a $C_{1-4}$ alkyl or alkoxy radical which is unsubstituted or substituted by a fluorine atom; and a silyl radical of the formula —Si—$(R^{15})_3$; wherein each $R^{15}$ is independently selected from the group consisting of a hydrogen atom and a $C_{1-4}$ alkyl radical; and (B) compounds of the formula $[(R^{18})_t ZH]^+[B(R^{14})_4]^-$ wherein B is a boron atom, H is a hydrogen atom, Z is a nitrogen atom or phosphorus atom, t is 2 or 3 and $R^{18}$ is independently selected from the group consisting of $C_{1-18}$ alkyl radicals, a phenyl radical which is unsubstituted or substituted by up to three $C_{1-4}$ alkyl radicals, or one $R^{18}$ taken together with the nitrogen atom may form an anilinium radical and $R^{14}$ is as defined above; and (C) compounds of the formula $B(R^{14})_3$ wherein $R^{14}$ is as defined above.

The "ionic activator" may abstract one activatable ligand so as to ionize the catalyst center into a cation, but not to covalently bond with the catalyst and to provide sufficient distance between the catalyst and the ionizing activator to permit a polymerizable olefin to enter the resulting active site.

Examples of ionic activators include:
triethylammonium tetra(phenyl)boron,
tripropylammonium tetra(phenyl)boron,
tri(n-butyl)ammonium tetra(phenyl)boron,
trimethylammonium tetra(p-tolyl)boron,
trimethylammonium tetra(o-tolyl)boron,
tributylammonium tetra(pentafluorophenyl)boron,
tripropylammonium tetra(o, p-dimethylphenyl)boron,
tributylammonium tetra(m,m-dimethylphenyl)boron,
tributylammonium tetra(p-trifluoromethylphenyl)boron,
tributylammonium tetra(pentafluorophenyl)boron,
tri(n-butyl)ammonium tetra(o-tolyl)boron,
N,N-dimethylanilinium tetra(phenyl)boron,
N,N-diethylanilinium tetra(phenyl)boron,
N,N-diethylanilinium tetra(phenyl)n-butylboron,
di-(isopropyl)ammonium tetra(pentafluorophenyl)boron,
dicyclohexylammonium tetra(phenyl)boron,
triphenylphosphonium tetra(phenyl)boron,
tri(methylphenyl)phosphonium tetra(phenyl)boron,
tri(dimethylphenyl)phosphonium tetra(phenyl)boron,
tropillium tetrakispentafluorophenyl borate,
triphenylmethylium tetrakispentafluorophenyl borate,
tropillium phenyltrispentafluorophenyl borate,
triphenylmethylium phenyltrispentafluorophenyl borate,
benzene (diazonium) phenyltrispentafluorophenyl borate,
tropillium tetrakis (2,3,5,6-tetrafluorophenyl) borate,
triphenylmethylium tetrakis (2,3,5,6-tetrafluorophenyl) borate, tropillium tetrakis (3,4,5-trifluorophenyl) borate,
benzene (diazonium) tetrakis (3,4,5-trifluorophenyl) borate,
tropillium tetrakis (1,2,2-trifluoroethenyl) borate,
triphenylmethylium tetrakis (1,2,2-trifluoroethenyl) borate,
tropillium tetrakis (2,3,4,5-tetrafluorophenyl) borate, and
triphenylmethylium tetrakis (2,3,4,5-tetrafluorophenyl) borate.

Readily commercially available ionic activators include: N,N-dimethylaniliniumtetrakispentafluorophenyl borate; triphenylmethylium tetrakispentafluorophenyl borate (tritylborate); and trispentafluorophenyl borane.

Ionic activators may also have an anion containing at least one group comprising an active hydrogen or at least one of any substituent able to react with the support. As a result of these reactive substituents, the ionic portion of these ionic activators may become bonded to the support under suitable conditions. One non-limiting example includes ionic activators with tris (pentafluorophenyl) (4-hydroxyphenyl) borate as the anion. These tethered ionic activators are more fully described in U.S. Pat. Nos. 5,834,393; 5,783,512; and 6,087,293.

The bulky ligand single site catalyst may be activated with a combination of aluminum compounds and ionic activators The phrase "and mixtures thereof" in relation to the catalyst mean the catalyst may be a mixture of one or more chromium catalysts, a mixture of one or more Ziegler-Natta catalysts, a mixture of one or more bulky ligand single site catalysts, a mixture of one or more chromium catalysts with one or more Ziegler Natta catalysts, a mixture of one or more Ziegler-Natta catalysts with one or more bulky ligand single site catalysts and a mixture of one or more chromium catalysts with one or more bulky ligand single site catalysts.

In a further embodiment the present invention provides a method to select initial set points for operating a plant to produce a resin having desired properties such as a specified PENT value. From the plot of known PENT values of resins produced under various conditions and the heat flow profile of the polymer on melting, the desired PENT value or range may be selected. However, as the plot includes values for resins made under known conditions it is also possible to interpolate between the conditions to conditions that will produce resins having PENT values close to the required PENT value to determine the initial set points for a plant run. This is particularly useful in setting experimental operating conditions for plant trials.

While the present invention has been described in terms of PENT values it could be used for other physical properties of polymers.

EXAMPLES

The present invention will now be illustrated by the following non limiting examples.

Example 1

Five high density polyethylene resins comprising 97 weight % ethylene and up to 3 weight % of hexene were prepared in a gas phase reactor using a sylil chromate catalyst supported on the same treated clay support and activated with diethyl aluminium ethoxide. The pent values for a pipe made from each of the resins was determined.

Then each of the resins was subject to a successive self nucleation and annealing. A small sample, typically 5.0±0.5 mg was placed in the sealed (crimped) pan of TA Instruments DSC Q 1000 thermal analyzer. The analyzer was operated using MDSC® Auto MFC Sw version 2.40 controller TA-5000 with Universal Analysis 2000.

Each sample was conditioned in the following manner to separate the various components having different crystallization temperatures.
1. equilibrate at 30.00° C.
2. isothermal for 1.00 min.
3. ramp+200.00° C./min to 200° C.
4. isothermal for 10.00 min
5. ramp−80.00° C./min to 135.00° C.
6. isothermal for 7 minutes
7. ramp−80.00° C./min to 20.00° C.
8. isothermal for 7 minutes
9. ramp+80.00° C./min to 130.00° C.
10. isothermal for 7 minutes
11. ramp−80.00° C./min to 20.00° C.
12. isothermal for 7 minutes
13. ramp+80.00° C./min to 125.00° C.
14. isothermal for 7 minutes
15. ramp−80.00° C./min to 20.00° C.
16. isothermal for 7 minutes
17. ramp+80.00° C./min to 120.00° C.
18. isothermal for 7 minutes
19. ramp−80.00° C./min to 20.00° C.
20. isothermal for 7 minutes
21. ramp+80.00° C./min to 110.00° C.
22. isothermal for 7 minutes
23. ramp−80.00° C./min to 20.00° C.
24. isothermal for 7 minutes
25. ramp+80.00° C./min to 100.00° C.
26. isothermal for 7 minutes
27. ramp−80.00° C./min to 20.00° C.
28. isothermal for 7 minutes
29. ramp+80.00° C./min to 90.00° C.
30. isothermal for 7 minutes
31. ramp−80.00° C./min to 20.00° C.
32. isothermal for 7 minutes
33. ramp+80.00° C./min to 80.00° C.
34. isothermal for 7 minutes
35. ramp−80.00° C./min to 20.00° C.
36. isothermal for 7 minutes.

The above conditioning fractionates the sample into components of various crystallization (melting) temperatures. This heating and cooling cycle is shown in FIG. 2.

Figure 3:
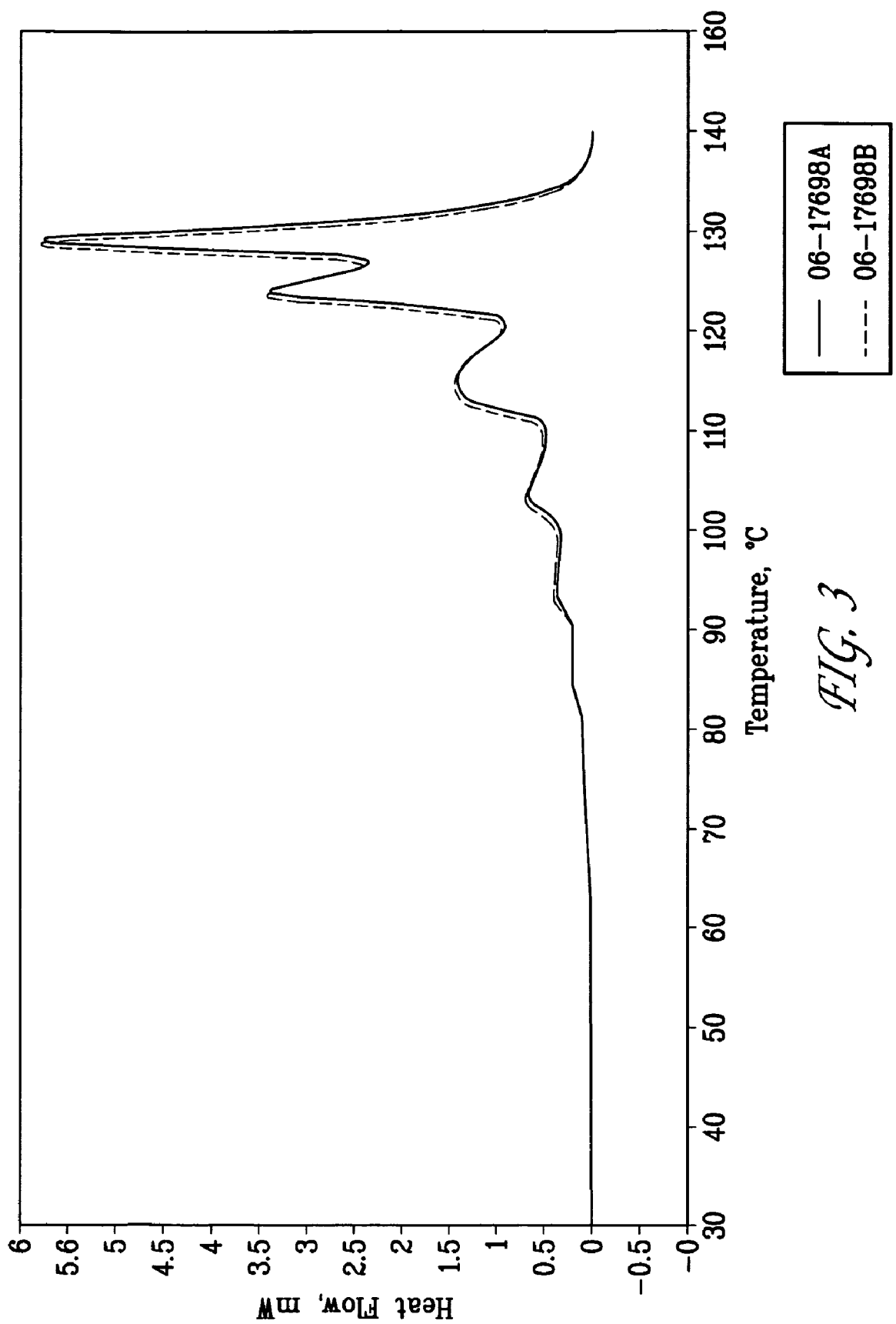
FIG. 3 is a plot of a heat flow curve (W/g) against temperature when melting a sample that has been subjected to successive self nucleation and annealing.

The sample was then melted using a ramp+20.00° C./min to 155.00° C. while the heat flow to melt the sample is measured. A resulting plot of heat flow (W/g) against temperature is shown in FIG. 3. In FIG. 3 the inflection point in the "valley" at about 120° C. is taken as the dividing line between the lower melting polymer component and the higher melting component. Then using the data it is possible to integrate the total heat flow to melt the sample and the heat flow to melt below the inflection point and/or above the inflection point to determine the % of heat capacity of the sample on either side of the inflection (set) point.

Figure 1:
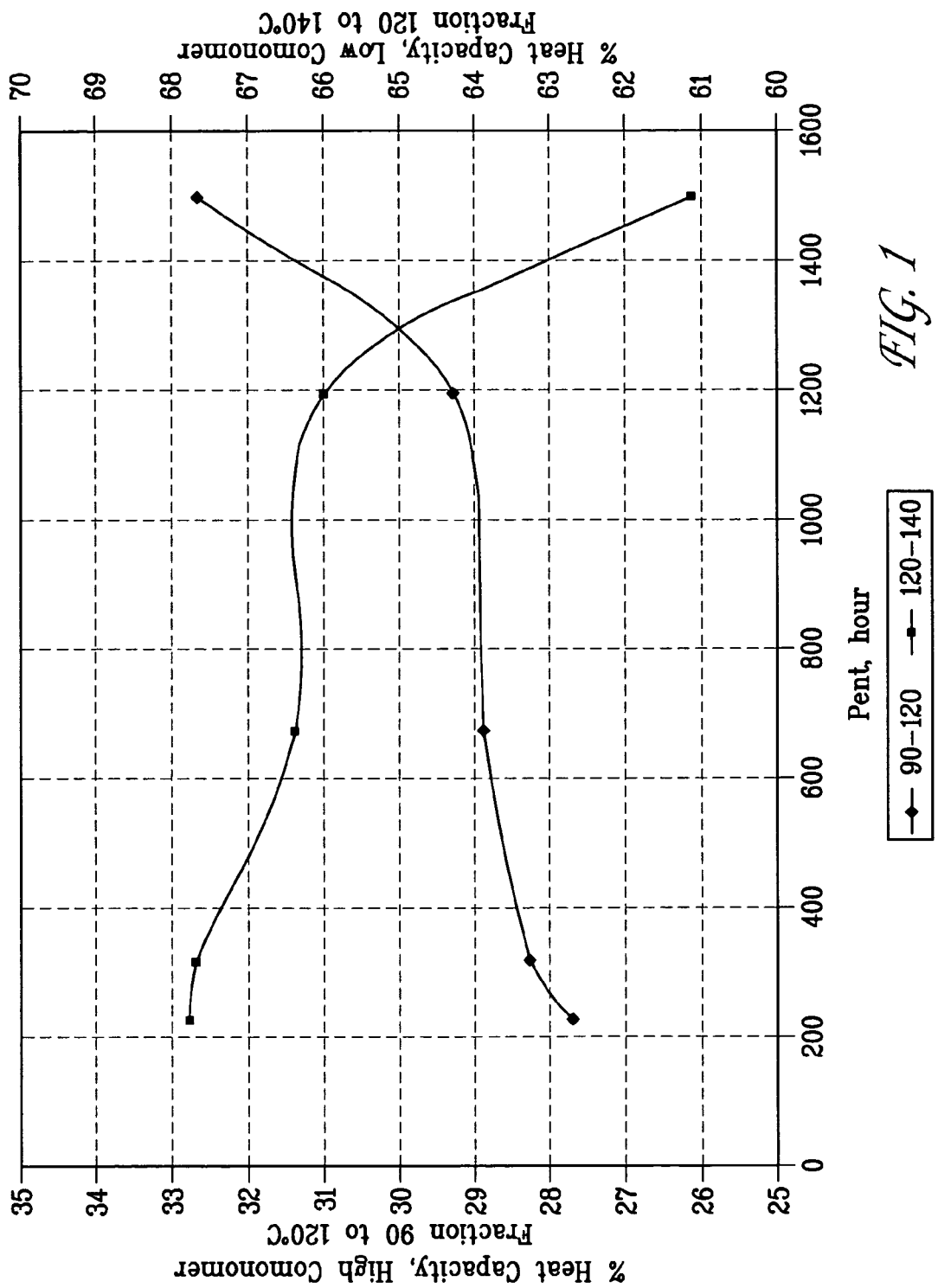
FIG. 1 is a graph showing the correlation between PENT values and the heat capacity of the polymer content having a high comonomer concentration (90° C. to 120° C.) and the heat capacity of the polymer content having a low comonomer content (120° C. to 140° C.).

In this example a plot was then made of the % of heat capacity of the portions of the sample as a function of PENT value for the polymer. This is shown in FIG. 1.

The plot may be used directly to predict the PENT value for a sample of polymer (polyethylene) made with the same catalyst system which has been tested using the self nucleating and annealing procedure described above or the plot may be converted to an algorithm to predict the PENT value of a sample of polymer made with the same catalyst system which has been tested using the self nucleating and annealing procedure described above.

Example 2

The flow index ($I_2$ according to ASTM D 1238-04c condition 190/2.16) was then determined for each of the polymer samples.

Using the % heat capacity above the inflection point (120° C.) (this is believed to be the high molecular weight homopolymer fraction or component of the polymer) the flow index values and the PENT values for the sample, an algorithm was developed to predict PENT values.

The algorithm was $$\text{Ln (predicted PENT value)} = a + bx^3 + cy \text{ wherein}$$

a, b, and c are constants derived from the curve fitting the data (a=23.972, b=−0.00056, and c=−0.273), x is the flow index of the polymer in g/10 minutes (ASTM 1238-04c condition 190/2.16) and y is the percentage of heat flow for melting the polymer above 120° C. The predicted values for the PENT test were within from about 1 to 5% of the actual values.

The curve for predicted PENT values were also fit to an algorithm to include the Rosland melt strength at 120° C. in cN. The form of the algorithm was $\text{PENT} = e^{(a+bx+cy+dz)}$ wherein a, b, c, x and y are as defined above and d is the Rosland Melt strength measured at 200° C. in cN. In this equation for the same catalyst system a is 19.401; b is −0.1491; c is −0.2192 and d is 0.0532. Again the predicted or calculated PENT value from this algothrim was within 5% of the measured value.

This demonstrates the procedure is suitable for the prediction of PENT values.

The present procedure may be used as a quality control at plants for resins that will be sold into the pressure pipe market.

What is claimed is:

1. A process to predict the PENT value of a resin prepared using a specific catalyst system comprising determining the PENT values for a number of different resins prepared using the specific catalyst system, determining for each of the resins for which a PENT value was determined one or more of:
   1) the percent of the heat capacity to melt the fraction of the polymer over the range from 90° C. to a set point relative to melting the entire sample at a heat up rate of 15 to 25° C. per minute which sample has been conditioned by successive self nucleation and annealing over the temperature range from 30 to 150° C. by heating and cooling the sample at a fixed rate from 70 to 95° C. per minute over the temperature range in decreasing increments of upper temperature from 5 to 10° C. provided that at least one increment is the set point; and
   2) the percent of the heat capacity to melt the fraction of the polymer over the range from a set point to 140° C. relative to melting the entire sample at a heat up rate of 15 to 25° C. per minute which sample has been conditioned by successive self nucleation and annealing over the temperature range from 30 to 150° C. by heating and cooling the sample at a fixed rate from 70 to 95° C. per minute over the temperature range in decreasing increments of upper temperature from 5 to 10° C. provided that at least one increment is the set point;

and plotting the results of the % heat capacity of 1, 2 or both as a function of the PENT values to generate a calibration curve.

2. The process according to claim 1, wherein the heat up rate to finally melt the polymer sample is from 18° C. to 22° C. per minute.

3. The process according to claim 2, wherein the heating and cooling rate for the successive self nucleation and annealing is from 75 to 85° C. per minute.

4. The process according to claim 1 wherein the set point is between 118° C. and 122.5° C.

5. The process according to claim 4, wherein during conditioning the sample is held at the various temperatures for a period from 5 to 10 minutes before the next temperature change.

6. The process according to claim 5, wherein during the successive self nucleation and annealing step is conducted over from 6 to 15 heating and cooling cycles.

7. The process according to claim 6, wherein the resin has a density from 0.940 to 0.970 g/cc.

8. The process according to claim 7, wherein the resin comprises from 95 to 99.9 weight % of ethylene and from 0.1 to 5 weight % of one or more $C_{4-8}$ alpha olefin monomers.

9. The process according to claim 8, wherein the set point is from 120° C. to 122° C.

10. The process according to claim 9, wherein the plot of % heat capacity of the sample as a function of PENT value is converted to an algorithm.

11. The process according to claim 10, wherein in the algorithm further includes a term for the melt index of the resin.

12. A method to select initial set point operating conditions for a plant producing polyolefins resins for use in pressure pipe applications comprising determining the PENT value for the resin according to claim 1, and then from the operating conditions used to generate the resins for the PENT plot selecting conditions which are expected to generate the resin having the required PENT value.

* * * * *